(12) United States Patent
Svojanovsky

(10) Patent No.: US 8,608,633 B2
(45) Date of Patent: Dec. 17, 2013

(54) SYSTEM FOR RECORDING ELECTRIC SIGNALS FROM A SUBJECT WHILE MAGNET FIELD PULSES ARE BEING APPLIED TO THE SUBJECT

(75) Inventor: Alexander Svojanovsky, Gilching (DE)

(73) Assignee: Brain Products GmbH, Gilching (DE)

(*) Notice: Subject to any disclaimer, the term of this patent is extended or adjusted under 35 U.S.C. 154(b) by 411 days.

(21) Appl. No.: 13/017,061

(22) Filed: Jan. 31, 2011

(65) Prior Publication Data
US 2012/0197089 A1  Aug. 2, 2012

(51) Int. Cl.
*A61N 2/04* (2006.01)
(52) U.S. Cl.
USPC ............... 600/14; 600/301; 600/545
(58) Field of Classification Search
USPC ............... 600/13, 14, 544, 545, 301
See application file for complete search history.

(56) References Cited

U.S. PATENT DOCUMENTS

2002/0055687 A1* 5/2002 Lutz .................. 600/544
2004/0138578 A1* 7/2004 Pineda et al. .......... 600/544

OTHER PUBLICATIONS

Allen, Philip J., et al., "A Method for Removing Imaging Artifact from Continuous EEG Recorded during Functional MRI," Academic Press, NeuroImage, vol. 12, pp. 230-239, 2000.

* cited by examiner

*Primary Examiner* — Christine Matthews
*Assistant Examiner* — Joshua D Lannu
(74) *Attorney, Agent, or Firm* — Laurence A. Greenberg; Werner H. Stemer; Ralph E. Locher

(57) ABSTRACT

A first apparatus applies magnetic field pulses to a subject, a second apparatus records electric signals of the subject, wherein the electric signals are received as analog signals from the subject while the magnetic field pulses are being applied to the subject. The first apparatus has a generating unit for generating the magnetic field pulses, a first clock generator for generating a first clock, and a first control unit for triggering generation of the magnetic field pulses by the generating unit with a fixed repetition rate based on the first clock. The second apparatus has an analog-to-digital conversion unit for converting the analog signals to corresponding digital signals by sampling each of the analog signals with a sampling rate, a second clock generator for generating a second clock, and a second control unit for causing the analog-to-digital conversion unit to set the sampling rate based on the second clock. A synchronizing unit synchronizes the second clock with the first clock.

5 Claims, 4 Drawing Sheets

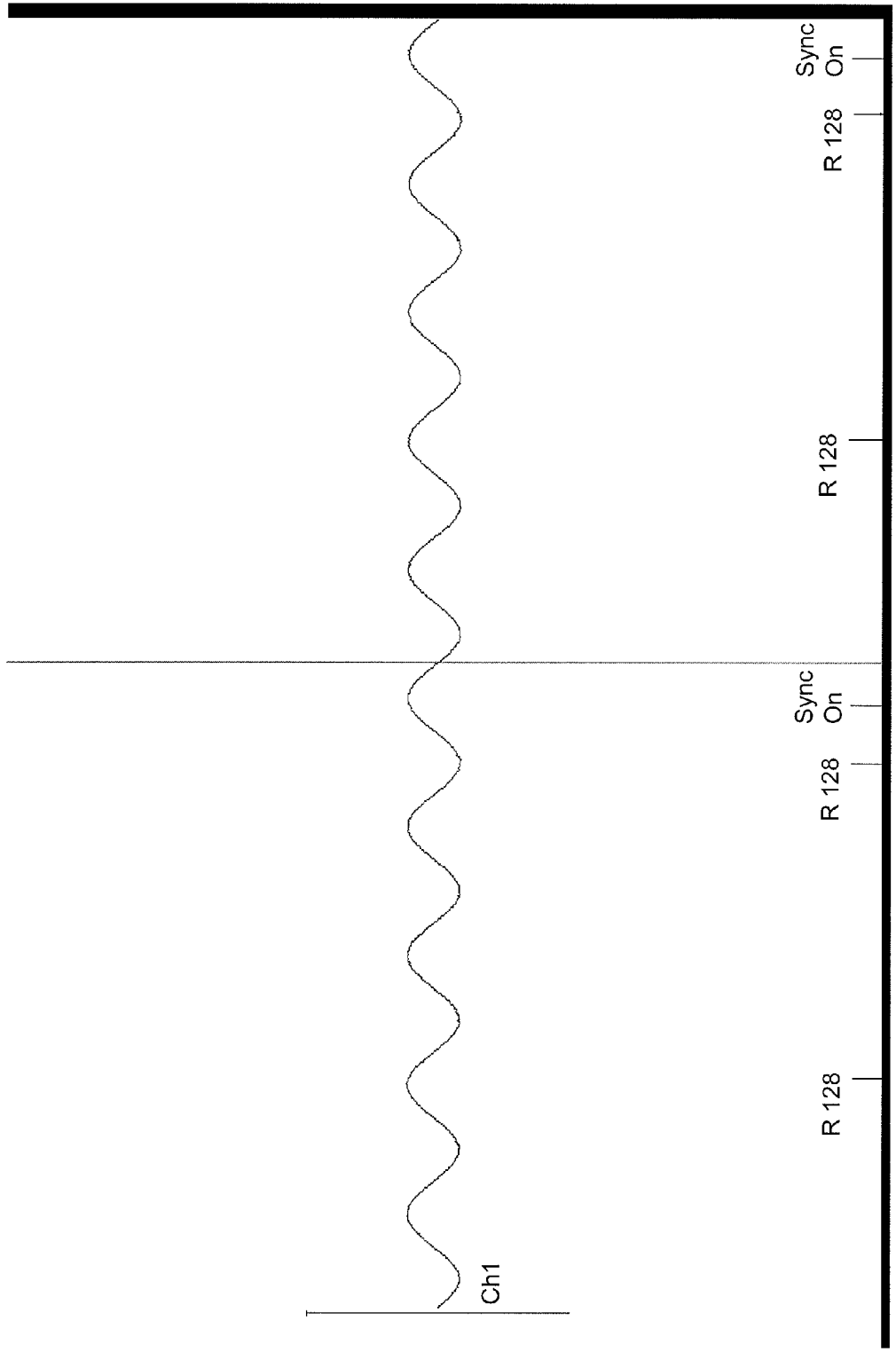

SYSTEM FOR RECORDING ELECTRIC SIGNALS FROM A SUBJECT WHILE MAGNET FIELD PULSES ARE BEING APPLIED TO THE SUBJECT

BACKGROUND OF THE INVENTION

Field of the Invention

The present invention relates to a system for recording electric signals from a subject while magnetic field pulses are being applied to the subject.

For example, electric signals are recorded from a patient's head by way of electrodes placed on the patient's head while magnetic field pulses are applied to the patient's head by a transcranial magnetic stimulation (TMS) apparatus. The recording of the electric signals is disturbed by the repeatedly applied magnetic field pulses.

One method of removing repeatedly occurring interferences/artifacts induced by a functional MRI (magnetic resonance imaging) in continuous EEG (electroencephalography) signals is the average subtraction method, described by Allen, Josephs, and Turner: "A Method for Removing Imaging Artifact from Continuous EEG Recorded During Functional MRI," Academic Press, NeuroImage vol. 12, pp. 230-39, 2000.

SUMMARY OF THE INVENTION

It is accordingly an object of the invention to provide an apparatus and system for recording electric signals in the context as described above which overcomes the above-mentioned disadvantages of the heretofore-known devices and methods of this general type and which provides for the correction of electric signals recorded from a subject, which suffer from interferences/artifacts caused by a TMS apparatus repeatedly applying magnetic field pulses to the subject during recording of the electric signals from the subject.

With the foregoing and other objects in view there is provided, in accordance with the invention, a system, comprising:

a first apparatus for applying magnetic field pulses to a subject, said first apparatus including:

a generating unit configured to generate the magnetic field pulses;

a first clock generator configured to generate a first clock; and a first control unit connected to said generating unit and to said first clock generator, and configured to trigger a generation of the magnetic field pulses by said generating unit with a fixed repetition rate based on the first clock;

a second apparatus for recording electric signals of the subject, wherein the electric signals are received as analog signals from the subject while the magnetic field pulses are being applied to the subject, said second apparatus including:

an analog-to-digital conversion unit configured to convert the analog signals to corresponding digital signals by sampling each of the analog signals with a sampling rate;

a second clock generator configured to generate a second clock; and a second control unit configured to cause said analog-to-digital conversion unit to set the sampling rate based on the second clock; and a synchronizing unit configured to synchronize the second clock with the first clock.

In other words, the objects are achieved by the claimed invention, which pertains to a system that comprises the first apparatus as claimed, the second apparatus as claimed, and a synchronizing unit as claimed.

In accordance with an added feature of the invention, the first apparatus may further comprise a clock output configured to output the first clock. The synchronizing unit may receive the first clock signal output from the clock output.

The synchronizing unit may further obtain the second clock from the second apparatus and control the second clock generator via a phase locked loop circuitry to synchronize the second clock continuously with the first clock.

The first apparatus may further comprise a trigger output configured to output a trigger signal and the second apparatus may further comprise a trigger input configured to receive the trigger signal, wherein the trigger signal indicates the time of generation of each of the magnetic field pulses by the generating unit.

The first apparatus may be a transcranial magnetic stimulation apparatus and the magnetic field pulses may be transcranial magnetic stimulation pulses, and the second apparatus may be an electroencephalography apparatus, an electrooculography apparatus, and an electrocardiography apparatus and the electric signals respectively may be electroencephalography signals, electrooculography signals and electrocardiography signals.

In accordance with an additional feature of the invention, the first apparatus is a transcranial magnetic stimulation apparatus and the magnetic field pulses are transcranial magnetic stimulation pulses, the second apparatus is an electroencephalography apparatus and the electric signals are electroencephalography signals, the subject is a patient's head, the generating unit comprises a stimulation coil configured to apply the transcranial magnetic stimulation pulses to the patient's head, and the second apparatus further comprises electrodes placed on the patient's head configured to receive the electroencephalography signals, and an amplifier configured to amplify the received electroencephalography signals and transmit the amplified electroencephalography signals to the analog-to-digital conversion unit.

In accordance with a concomitant feature of the invention, the synchronizing unit may be part of the second apparatus.

With the inventive features, artifacts introduced by TMS pulses can be completely removed from an EEG signal.

Other features which are considered as characteristic for the invention are set forth in the appended claims.

Although the invention is illustrated and described herein as embodied in a system for recording electric signals from a subject while magnetic field pulses are applied to the subject, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 4 shows a time chart illustrating a corrected sine wave signal obtained by correcting the sine wave signal of FIG. 2 using the average subtraction method in a system according to an embodiment of the invention.

DETAILED DESCRIPTION OF THE INVENTION

Figure 1:
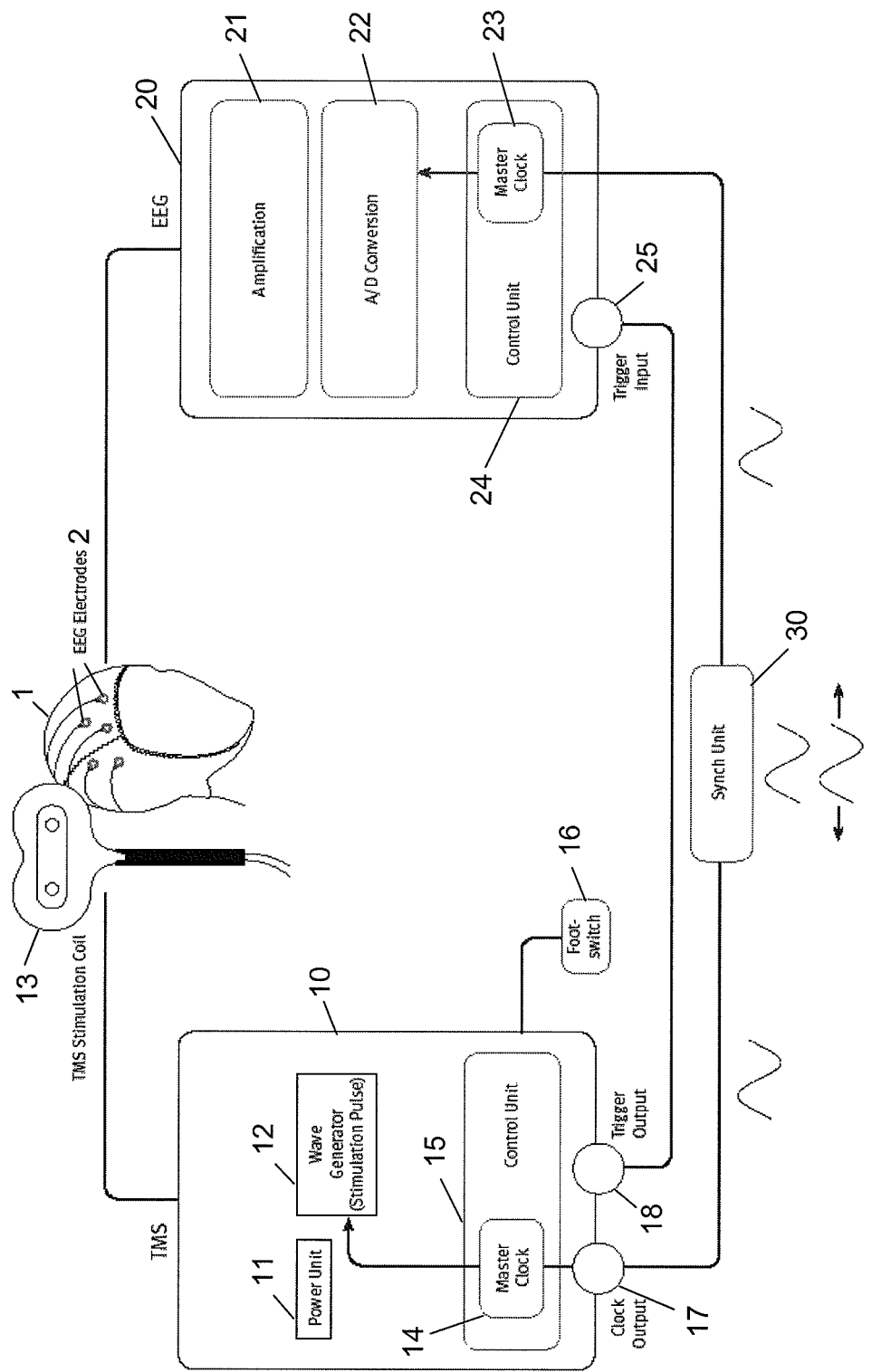
FIG. 1 is a schematic block diagram illustrating an embodiment of the invention of a system for recording electric signals from a subject during the application of magnetic field pulses to the subject.

Referring now to the figures of the drawing in detail and first, particularly, to FIG. 1 thereof, electric signals are recorded from a subject's/patient's head 1 by way of EEG electrodes 2 placed on the patient's head 1. At the same time, a TMS apparatus 10 applies magnetic field pulses to the patient's head 1. The recording of the electric signals is disturbed by the magnetic field pulses.

The TMS apparatus 10 comprises a power unit 11, a wave generator 12 and a TMS stimulation coil 13 for generating the magnetic field pulses. By placing the TMS stimulation coil 13 near the patient's head 1 the generated magnetic field pulses are applied to the patient's head 1. The TMS apparatus 10 further comprises a master clock generating unit (TMS master clock generating unit) 14 which generates a master clock (TMS master clock). Based on the TMS master clock the magnetic field pulses are repeatedly generated with a fixed repetition rate and applied by the TMS apparatus 10 to the patient's head 1. A control unit (TMS control unit) of the TMS apparatus 10, which may comprise the TMS master clock generating unit 14, performs control of the TMS apparatus 10. The TMS apparatus may further comprise a footswitch 16 to be pressed by a user during operation of the TMS apparatus 10 to comply with safety regulations.

While the magnetic field pulses are repeatedly applied to the patient's head 1, the EEG electrodes 2 receive continuous analog electric signals from the patient's head 1, which are fed to an EEG apparatus 20. An amplification unit 21 of the EEG apparatus 20 amplifies the continuous analog electric signals, and an analog-to-digital conversion unit 22 of the EEG apparatus 20 converts the continuous analog electric signals to corresponding digital signals by sampling the continuous analog electric signals with a sampling rate which is set based on a master clock (EEG master clock) generated by a clock generating unit (EEG clock generating unit) 23 of the EEG apparatus 20. A control unit (EEG control unit) 24 of the EEG apparatus 20, which may comprise the EEG clock generating unit 23, performs control of the EEG apparatus 20.

As mentioned before, a method of correcting artifacts induced by a functional MRI in recorded EEG signals is the average subtraction method. According to that method, segments including a predetermined number of samples of a digital signal obtained from the analog-to-digital conversion unit 22, which are sampled starting at respective stimulation times of applying the magnetic field pulses, are averaged and the averaging result is subtracted from the segments.

However, as the TMS apparatus 10 and the EEG apparatus 20 are controlled by different and independent master clocks, there may be no fixed time-lag between the stimulation times and sampling times of the samples. A way of overcoming this problem is to perform analog-to-digital conversion by the EEG apparatus 20 with a sampling rate which is a multiple (e.g. 100 MHz) of the TMS master clock. This, however, is not practical.

Figure 2:
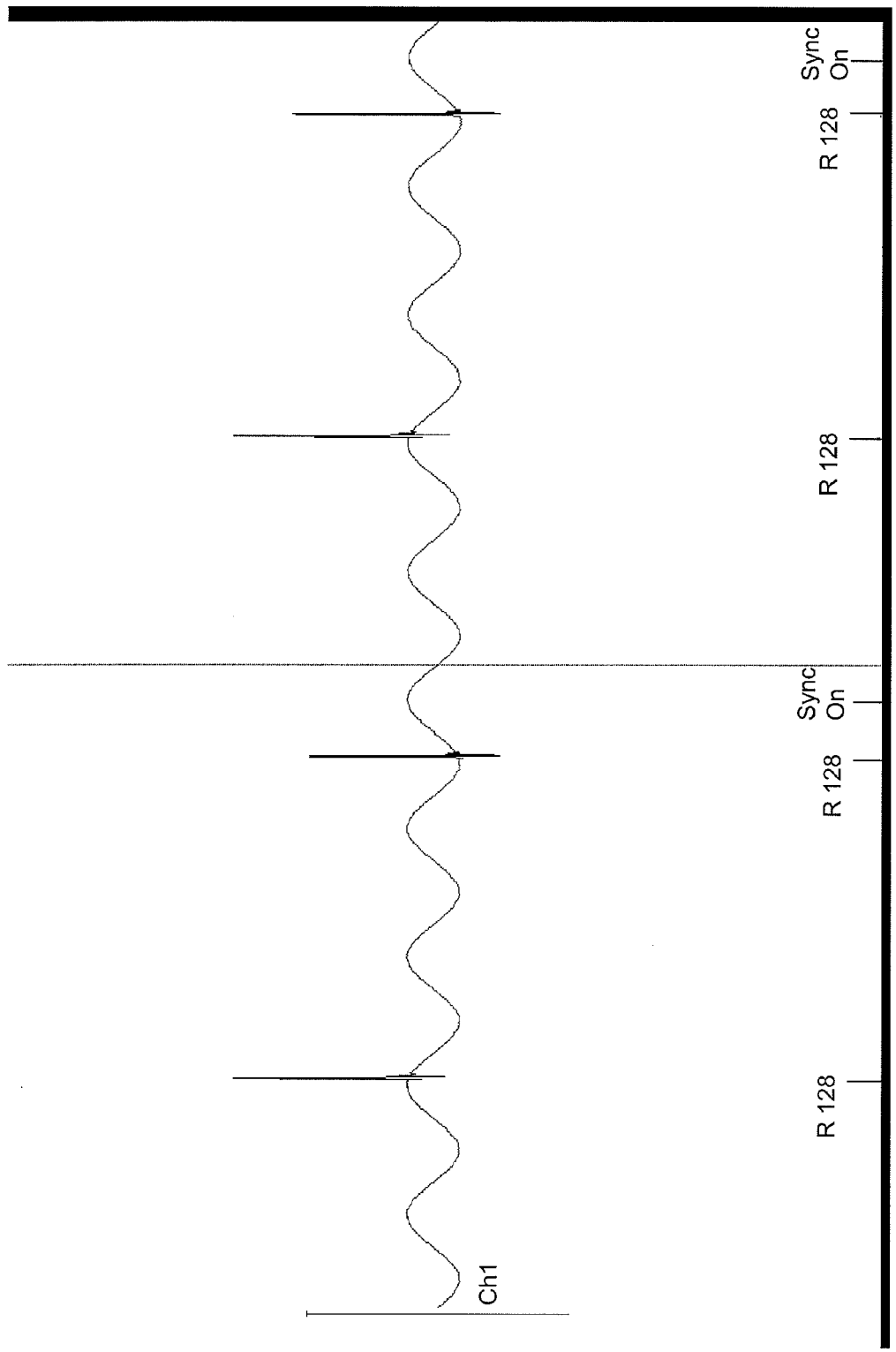
FIG. 2 shows a time chart illustrating a sine wave signal as an EEG signal, including artifacts caused by TMS pulses.

FIG. 2 shows a sine wave signal as EEG signal recorded by means of an EEG electrode according to a channel 1, which is placed on a patient's head. TMS pulses (magnetic field pulses) have been fired at the sine wave signal at times marked with R128 (stimulation time). Thus, the sine wave signal shows artifacts induced by the TMS pulses around the times R128.

Figure 3:
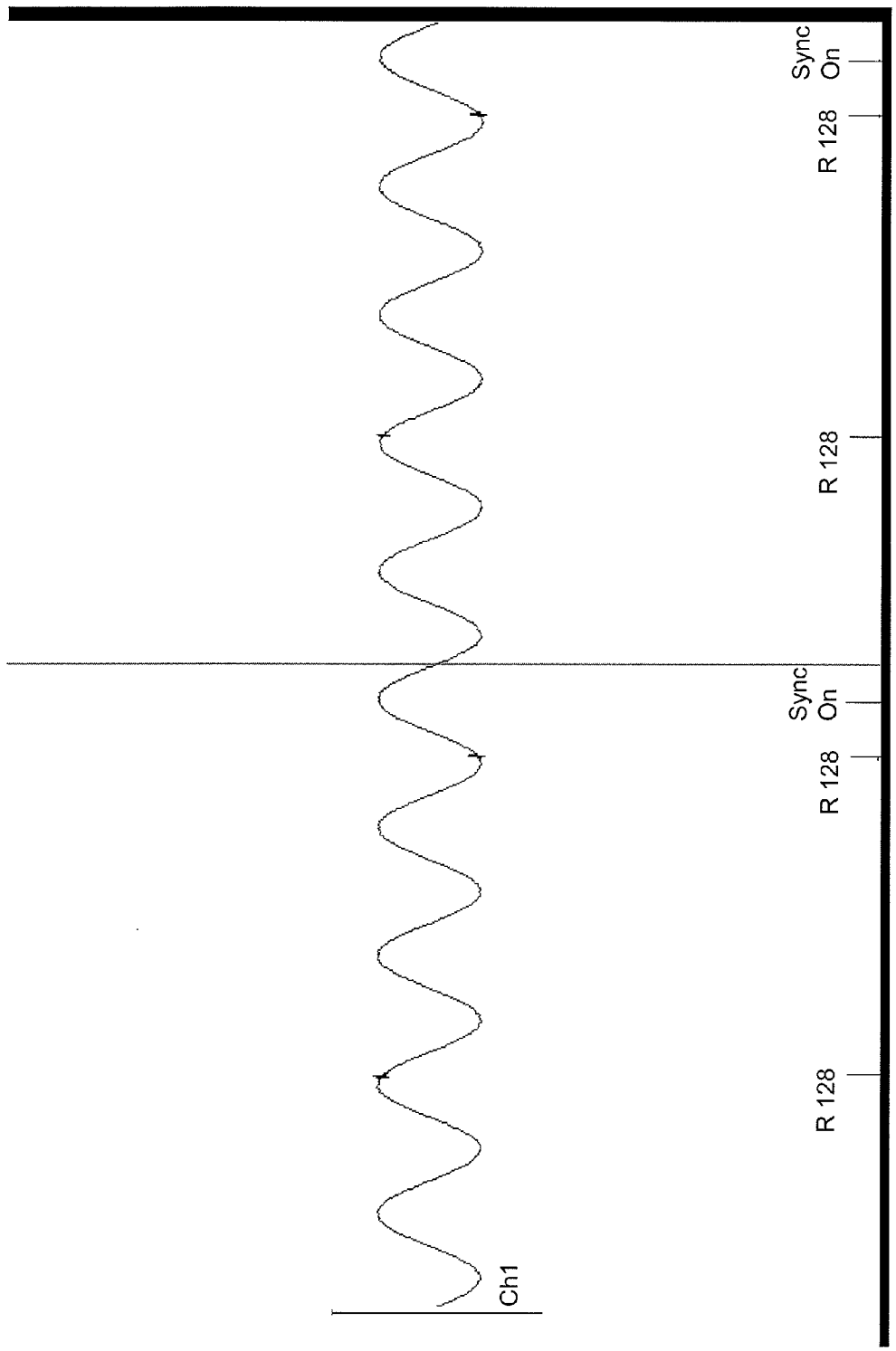
FIG. 3 shows a time chart illustrating a corrected sine wave signal obtained by correcting the sine wave signal of FIG. 2 using the average subtraction method in a system with independent TMS and EEG master clocks.

With the independent TMS and EEG master clocks, when applying the average subtraction method for removing the artifacts from the sine wave signal shown in FIG. 2, a sine wave signal as illustrated in FIG. 3 is obtained. It can be seen that the artifacts are not completely removed. Rather, sharp/high frequency steps are present in the sine wave signal around the times R128 due to the variable phase shift between the stimulation times and the sampling times. Such sharp/high frequency steps in an electric signal recorded from a patient's head render an electroencephalogram useless. It is to be noted that the scale of FIG. 3 differs from that of FIGS. 2 and 4, i.e. is larger than that of FIGS. 2 and 4 in order to make the artifacts visible.

Returning to FIG. 1, the TMS apparatus 10 comprises a clock output 17 which outputs the TMS master clock to a synchronizing unit 30. The synchronizing unit 30 also obtains the EEG master clock from the EEG apparatus 20 and controls the EEG master clock generator 23, e.g. using a phase locked loop (PLL) circuitry, to continuously synchronize the EEG master clock with the TMS master clock. The synchronizing unit 30 may be part of the EEG apparatus 20.

The TMS apparatus 10 further comprises a trigger output 18 which outputs a trigger signal to the EEG apparatus 20 comprising a trigger input 25 which receives the trigger signal. The trigger signal indicates the stimulation times, i.e. the times at which the TMS pulses are generated and applied to the patient's head 1.

With synchronizing the phases of the TMS and EEG master clocks, the analog-to-digital conversion by the analog-to-digital conversion unit 22, i.e. the sampling rate, can be aligned with the TMS master clock and, hence, with the stimulation times of generating and applying the TMS pulses.

The EEG apparatus 20 sets the stimulation times input to the trigger input 25 as a timing marker. The TMS apparatus 10 stimulates (i.e. generates and applies the TMS pulses) with a fixed repetition rate, e.g. 10 Hz. With the phase synchronization of the TMS and EEG master clocks, among stimulation times, sampling times have the same time-lag to the stimulation times. In other words, assuming a first and a second stimulation time and a first sampling time which occurs first after the first and second stimulation times, the time-lag between the first stimulation time and the first sampling time and the time-lag between the second stimulation time and the first sampling time are the same.

In contrast, without a synchronization of the phases of the TMS and EEG master clocks, the above-mentioned time-lags may be different.

FIG. 4 shows a corrected sine wave signal obtained by correcting the sine wave signal of FIG. 2 using the average subtraction method in the system of FIG. 1. As can be seen from FIG. 4, the artifacts introduced by the TMS pulses can be completely removed from the sine wave signal.

The patient's head has to be fixed in order to avoid topographic offsets of the artifacts on EEG channels. The EEG apparatus 20 records data of the electric signals from the patient's head continually and phase synchronously to the TMS apparatus 10. The start of a stimulation sequence of the TMS apparatus 10 can be selected freely as the time linking of the TMS and EEG master clocks is stable as long as the TMS apparatus 10 and the EEG apparatus 20 remain synchronized by the synchronizing unit 30.

It is to be noted that the electric signal is not limited to an EEG signal, but also may comprise physiological parameters such as electrooculography signals and electrocardiography signals which are received from a subject by dedicated electrodes. In the case of recording electrooculography signals, the apparatus 20 receives and processes the electrooculography signals, and in the case of recording electrocardiography signals, the apparatus 20 receives and processes the electrocardiography signals similarly to EEG signals from the EEG electrodes 2.

It is to be understood that the above description is illustrative of the invention and is not to be construed as limiting the invention. Various modifications and applications may occur to those skilled in the art without departing from the true spirit and scope of the invention as defined by the appended claims.

The invention claimed is:

1. A system, comprising:
a first apparatus for applying magnetic field pulses to a subject, said first apparatus including:
  a generating unit configured to generate the magnetic field pulses;
  a first clock generator configured to generate a first clock;
  a clock output configured to output the first clock;
  a first control unit connected to said generating unit and to said first clock generator, and configured to trigger a generation of the magnetic field pulses by said generating unit with a fixed repetition rate based on the first clock;
a second apparatus for recording electric signals of the subject, wherein the electric signals are received as analog signals from the subject while the magnetic field pulses are being applied to the subject, said second apparatus including:
  an analog-to-digital conversion unit configured to convert the analog signals to corresponding digital signals by sampling each of the analog signals with a sampling rate;
  a second clock generator configured to generate a second clock; and
  a second control unit configured to cause said analog-to-digital conversion unit to set the sampling rate based on the second clock; and
a synchronizing unit connected to receive the first clock output from said clock output and configured to obtain the second clock from said second apparatus and control said second clock generator via a phase locked loop circuitry to continuously synchronize the second clock with the first clock.

2. The system according to claim 1, wherein said first apparatus comprises a trigger output configured to output a trigger signal and said second apparatus comprises a trigger input configured to receive the trigger signal, wherein the trigger signal indicates a time of generation of each of the magnetic field pulses by said generating unit.

3. The system according to claim 1, wherein said first apparatus comprises a transcranial magnetic stimulation apparatus and the magnetic field pulses are transcranial magnetic stimulation pulses, and wherein said second apparatus comprises an electroencephalography apparatus, an electrooculography apparatus or an electrocardiography apparatus, and the electric signals respectively comprise electroencephalography signals, electrooculography signals or electrocardiography signals.

4. The system according to claim 1, wherein:
said first apparatus is a transcranial magnetic stimulation apparatus and the magnetic field pulses are transcranial magnetic stimulation pulses;
said second apparatus is an electroencephalography apparatus and the electric signals are electroencephalography signals;
the subject is a patient's head;
said generating unit comprises a stimulation coil configured to apply the transcranial magnetic stimulation pulses to the patient's head; and
said second apparatus further comprises electrodes to be placed on the patient's head and configured to receive the electroencephalography signals, and an amplifier configured to amplify the electroencephalography signals received by said electrodes and to transmit amplified electroencephalography signals to said analog-to-digital conversion unit.

5. The system according to claim 1, wherein said synchronizing unit forms a part of said second apparatus.

* * * * *